(12) United States Patent
Ju

(10) Patent No.: US 8,148,108 B2
(45) Date of Patent: Apr. 3, 2012

(54) PROCESS FOR PRODUCING CELLULASE

(75) Inventor: Lu-Kwang Ju, Akron, OH (US)

(73) Assignee: The University of Akron, Akron, OH (US)

( * ) Notice: Subject to any disclaimer, the term of this patent is extended or adjusted under 35 U.S.C. 154(b) by 590 days.

(21) Appl. No.: 12/059,057

(22) Filed: Mar. 31, 2008

(65) Prior Publication Data

US 2008/0241885 A1    Oct. 2, 2008

Related U.S. Application Data

(60) Provisional application No. 60/920,942, filed on Mar. 30, 2007.

(51) Int. Cl.
  *C12N 15/00*    (2006.01)
  *C12N 9/42*     (2006.01)
  *A61K 8/00*     (2006.01)

(52) U.S. Cl. ............ 435/69.2; 424/94.61; 435/209

(58) Field of Classification Search .............. None
See application file for complete search history.

(56) References Cited

U.S. PATENT DOCUMENTS

| | | | |
|---|---|---|---|
| 5,616,479 | A | 4/1997 | Marchal et al. |
| 5,756,471 | A | 5/1998 | Hillion et al. |
| 5,767,255 | A | 6/1998 | Wullbrandt et al. |
| 6,433,152 | B1 | 8/2002 | Lang et al. |
| 2004/0171512 | A1 | 9/2004 | Furuta et al. |
| 2008/0076165 | A1* | 3/2008 | Gross et al. ............ 435/134 |

FOREIGN PATENT DOCUMENTS

WO   WO2007/073371 A1   6/2007

OTHER PUBLICATIONS

Davila, A.-M et al. Sophorose lipid fermentation with differentiated substrate supply for growth and production phases, Applied Microbiology and Biotechnology, 1997, vol. 47, pp. 496-501, especially abstract, introduction, and materials & methods, 1997.

Brakemeier, A. et al. *Candida bombicola*: production of novel alkyl glycosides based on glucose/2-dodecanol, Applied Microbiology and Biotechnology, 1998, vol. 50, pp. 161-166, especially abstract and materials & methods, 1998.

Rau U. et al. Sophorolipids: a source for novel compounds, Industrial Crops and Products, 2001, vol. 13, pp. 85-92, especially abstract, materials & methods, and conclusions.

Gross R.A. et al. Glycolipids from *Torulopsis bombicola*: Biosynthesis, lipase-selective modification and anti-cancer activity, Abstract, 217th American Chemical Society, 1999, National Meeting, Anaheim CA, Mar. 21-25, 1999, BIOT-181, ACS; Washington, DC.

Hrmova et al. Induction of cellulose- and xylan-degrading enzyme systems in *Aspergillus terrus* by homo- and hetrodisaccharides composed of glucose and xylose, Journal of General Microbiology, 1991, vol. 137, No. 3, pp. 541-547, especially abstract, 1991.

Bisht, K.S. et al., J. Org. Chem., vol. 64, pp. 780-789 (1999).

* cited by examiner

*Primary Examiner* — Michele K Joike

(74) *Attorney, Agent, or Firm* — Renner Kenner Greive Bobak Taylor & Weber

(57) ABSTRACT

Various methods for the production of cellulase are disclosed. In one embodiment the method for producing cellulase includes contacting a culture comprising a sophorolipid producer and a cellulase producer with a substrate that is consumed by the sophorolipid producer. In addition, a microorganism culture made from a sophorolipid producer and a cellulase producer is disclosed.

28 Claims, 4 Drawing Sheets

PROCESS FOR PRODUCING CELLULASE

FIELD OF THE INVENTION

Various methods for the production of cellulase are disclosed. In one embodiment the method for producing cellulase includes contacting a culture comprising a sophorolipid producer and a cellulase producer with a substrate that is consumed by the sophorolipid producer. In addition, a microorganism culture made from a sophorolipid producer and a cellulase producer is disclosed.

BACKGROUND OF THE INVENTION

Lignocellulosic materials are the most abundant biomass on earth. It can be converted to simple sugars and other useful products. One example of a potential product is bioethanol, which can be used as an alternative renewable fuel. An effective and environment-friendly approach of converting lignocellulosic materials involves the usage of cellulase enzymes, which catalyze the hydrolysis reactions of the polymeric lignocellulosic materials. However, microbial production of cellulase is regulated by complex gene-level induction and repression mechanisms. This complex regulation causes the production process to be expensive and difficult to operate and/or control. For example, currently the most commonly used inducing substrate is lactose, a disaccharide of glucose and galactose. When added at low concentrations, the inducing efficiency of lactose is sub-optimal. When added at slightly higher concentrations, the glucose formed by the hydrolysis of lactose starts to repress the expression of cellulase genes. That is, the glucose slows or stops the continual synthesis of cellulase.

It is known that the glucose repression occurs at low glucose concentrations. Lactose-based production is therefore hard to control. The difficulties of lactose-based production of cellulase prompted the development of genetically engineered microorganisms to be used for industrial cellulase production. This approach carries serious ecological and environmental risks. Plants rely on the difficulty of cellulase hydrolysis as their first line of defense for microbial attacks.

To meet the possible energy demand from biomass-derived fuel, the industrial biomass conversion will have to occur in very large scales and at widespread production and/or processing sites. Accidental release of large quantities of the genetically engineered microorganisms from these processes could possibly occur. The ecological and environmental effects of the release are unknown but potentially disastrous because a widespread increase in microbial ability of cellulase production may have seriously damaging effects on all plants. A problem is therefore that the use of genetically engineered microorganisms can result in serious ecological and environmental risks.

Sophorose is known to be another inducer for cellulase synthesis. However, its usage in industrial cellulase production has so far been considered infeasible because of its extremely high price. Sophorolipids are glycolipids produced by some yeasts. The various processes for sophorolipid production have been studied and reported.

Earlier work in the field has shown sophorose as an acceptable inducer of cellulase protein but commercialization proves impractical due to cost. See Hrmova, M., Petrakova, E., Biely, P., Journal of General Microbiology 137, 541-547 (1991). In another filing Gross et al. disclosed the use of sophorolipids for protein production. In WO2007/073371, Gross et al., detail the synthesis of sophorlipids with protein inducer and/or repressor activities by fermenting *Candida bombicola* in a fermentation medium to form a mixture of lactonic and non-lactonic sophorolipids. Again the drawback to this method involves the costs associated with collection, separation and potentially purification of the sophorolipids produced.

Therefore, processes for cellulase production that are effective and economical, as well as those which circumvent complex regulation and use non-genetically-engineered microorganisms, are therefore desirable to the biomass conversion and utilization industry.

SUMMARY OF INVENTION

The present invention provides for various processes for the production of cellulase utilizing sophorolipid-containing broth for induction. In one embodiment, the process for producing cellulase comprises exposing a sophorolipid producer and a cellulase producer to a production medium which contains carbon substrates that promote sophorolipid production and do not repress cellulase production, at the employed concentrations.

In one embodiment of the present invention discloses a method for producing cellulase comprising: providing a culture comprising at least one sophorolipid producer and at least one cellulase producer, providing at least one substrate supported on a production medium, contacting the culture with the production medium and allowing the at least one substrate to be consumed by the at least one sophorolipid producer and the at least one cellulase producer to produce cellulase.

In another embodiment the present invention discloses a method for producing cellulase comprising: providing at least one sophorolipid producer in a first container, providing at least one substrate supported on a production medium to the first container and allowing the at least one substrate to be consumed by the at least one sophorolipid producer to produce a broth, providing at least one cellulase producer in a second container, providing the broth from the first container to the second container to produce a culture and allowing the culture to produce cellulase.

In yet another embodiment the present invention discloses a method for producing cellulase comprising: providing at least one sophorolipid producer in a first container, providing at least one substrate supported on a production medium to the first container and allowing the at least one substrate to be consumed by the at least one sophorolipid producer to produce a broth, providing at least one cellulase producer in a second container, providing the broth from the first container and the at least one cellulase producer from the second container to a third container to produce a culture and allowing the culture to produce cellulase.

In another embodiment the present invention discloses a microorganism culture comprising one or more sophorolipid producing organisms and one or more cellulase producing organisms wherein: the one or more sophorolipid producing organisms are *Candida bombicola, Starmerella bombicola, Candida apicola, Rhodotorula bogoriensis*, and *Wickerhamiella domericqiae*, and the one or more cellulase producing organisms are *Trichoderma reesei, Trichoderma viviride, Trichoderma longibrachiatum, Trichoderma lignorum, Aspergillus niger, Aspergillus terreus, Trametes trogii, Penicillium fellutanum, Penicillium hordei, Penicillium echinulatum, Aureobasidium pullulans, Rhizobium phaseoli, Humicola insolens, Piromyces communis, Clostridium thermocellum*, and *Themomonospora fusca*.

BRIEF DESCRIPTION OF THE FIGURES

The various embodiments of the present invention can be understood with reference to the following figures.

DETAILED DESCRIPTION

Figure 1:
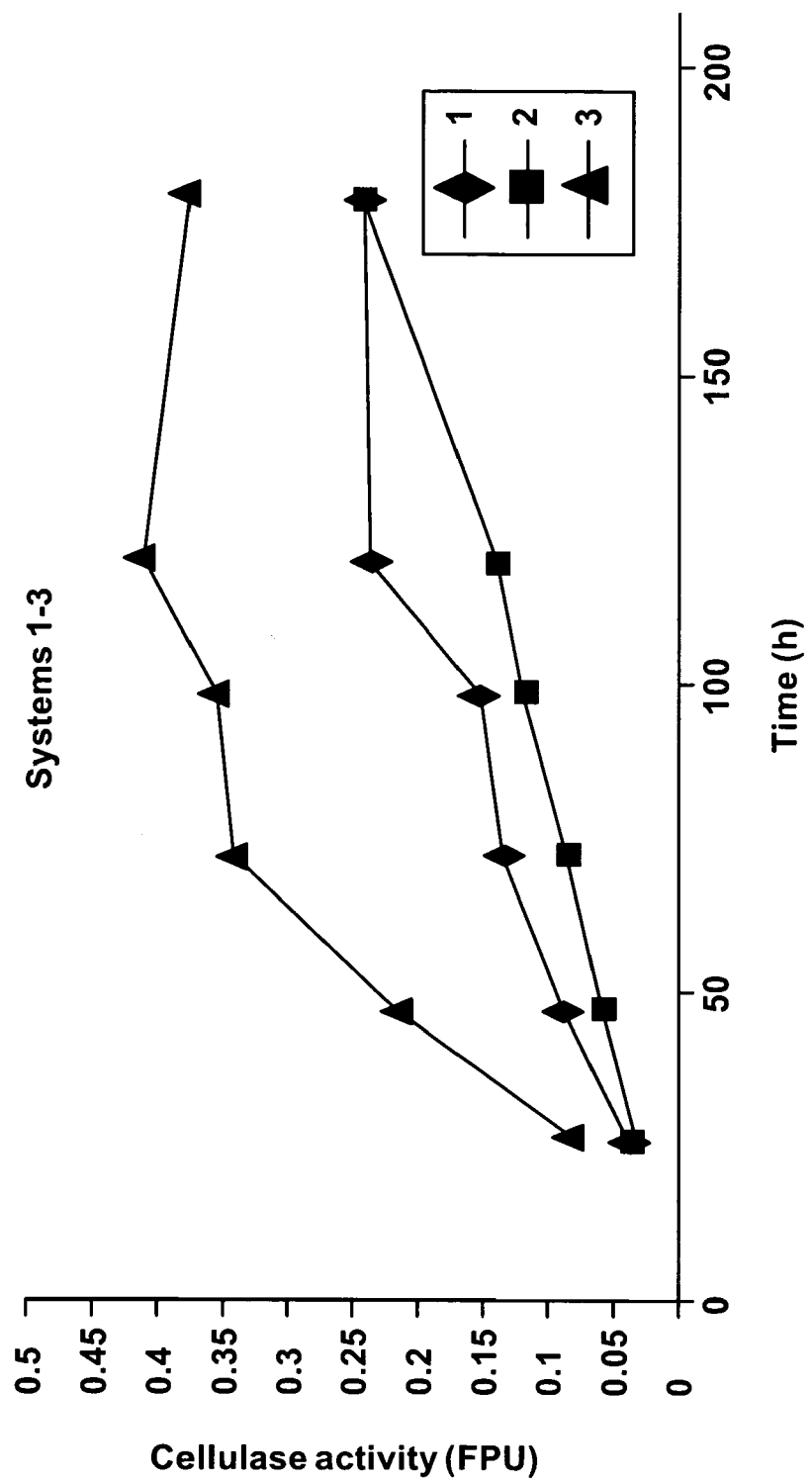
FIG. 1 provides plots of cellulase activity production from co-cultures of *Trichoderma reesei* and *Candida bombicola* in which the amount of *Trichoderma reesei* was approximately four times greater than the amount of *Candida bombicola*, according to an embodiment of the present invention.

The following terms are defined herein.

Filter paper unit (FPU) refers to the amount of enzyme that will cause 2.0 mg of reducing sugar equivalents to be released in 1 hour at 50° C. and a pH of 4.8.

"Without significantly affecting" refers to producing or promoting the production of compound A while not inhibiting or repressing the production of compound B at a level of more than about 20%, more than about 5%, more than about 1% and more than about 0.1%.

The present invention overcomes the complex biological induction and repression mechanisms encountered in the existent processes that use lactose, cellulase hydrolysate, solid cellulase powders or other substrates. The invention does not involve the use of genetically engineered microorganisms and avoids the serious ecological and environmental risks associated with such an approach. The invention allows economical production of cellulase from cheap substrates. For example, the glycerol used for the production can be the crude glycerol from biodiesel production. The primary impurities in crude biodiesel glycerol are fatty acids that facilitate the desired production of sophorolipids to induce more active cellulase production, according to an embodiment of the invention herein. The use of this crude biodiesel glycerol as substrate for cellulase production thus eliminates the purification costs required otherwise for producing a marketable glycerol product from the biodiesel manufacturing processes. The invention thus promotes the development of alternative renewable energy both in the usage of lignocellulosic materials and in the biodiesel production.

It has been found, according to various embodiments of the present invention, that the broth of a sophorolipid producer can be used for effective induction of cellulase production. Effective cellulase production can, for example, provide a source of renewable energy both in the usage of lignocellulosic materials and in the utilization of the biodiesel production by product, glycerol. The method for cellulase production includes contacting a culture which includes at least two organisms, a sophorolipid producer and a cellulase producer, with a production medium which contains carbon substrates that promote sophorolipid production and do not repress cellulase production, at the employed concentrations. The sophorolipid producer converts the substrate to sophorolipids. The produced sophorolipids are consumed by the cellulase producer, and therefore, induce the cellulase synthesis by the cellulase producer.

The sophorolipid producer includes, but is not limited to, *Candida bombicola, Starmerella bombicola* (potentially the teleomorph of *Candida bombicola*), *Candida apicola, Rhodotorula bogoriensis, Wickerhamiella domericqiae*, other species belonging or related to the *Wickerhamiella, Starmerella* and *Rhodotorula* clades, and the like, and mixtures thereof. The cellulase producer includes, but is not limited to, *Trichoderma reesei, Trichoderma viviride, Trichoderma longibrachiatum, Trichoderma lignorum, Aspergillus niger, Aspergillus terreus, Trametes trogii, Penicillium fellutanum, Penicillium hordei, Penicillium echinulatum, Aureobasidium pullulans, Rhizobium phaseoli, Humicola insolens, Piromyces communes, Clostridium thermocellum, Themomonospora fusca*, various other *Trichoderma* species, and the like, and mixtures thereof.

The carbon substrate can be any material that supports sophorolipid production and does not repress cellulase production, at the employed concentrations. For example the substrate can include, but is not limited to, glycerol, glucose, galactose, mannose, xylose, arabinose, lactose, sucrose, fructose, sorbose, maltose, cellobiose, amylase, amylopectin, dextrins, starch, glycogen, cellulose, various polysaccharides, sugar-containing materials, sugar-derived materials, yeast extract, peptone, tryptone, amino acids, peptides, proteins, milk, fatty acids, glycerides, hydrocarbons, various lipidic oils, and the like, and mixtures thereof as the primary carbon and energy source to support the metabolic activities of the microorganisms, and vegetable oil, rapeseed oil, palm oil, oleic acid, linoleic acid, palmitic acid, lauric acid, various fatty acids, milk, fat, glycerides, various hydrocarbons, alcohols, aldehydes, esters, ethers, amides, and the like, and mixtures thereof as the secondary carbon source to provide the lipid precursor for effective sophorolipid production.

As noted above, the sophorolipid producer converts the substrate to sophorolipids, and the amount of sophorolipid present can vary depending upon the at least two organisms that are used, and can have impact on the amount of cellulase produced. In one embodiment, the ratio of the sophorolipid producer to the cellulase producer ranges from about 10:1 to about 1:25, in another embodiment, from about 5:1 to about 1:10, and in another embodiment, from about 1:1 to about 1:4.

In another embodiment of the invention, the method for producing cellulase includes contacting a culture which includes *Candida bombicola*, a sophorolipid producer, and *Trichoderma reesei*, a cellulase producer to a production medium. In one embodiment, the ratio of *Candida bombicola* to the *Trichoderma reesei* ranges from about 10:1 to about 1:25, in another embodiment, from about 5:1 to about 1.10, and in another embodiment, from about 1:1 to about 1:4.

In another embodiment, the production medium of any of the embodiments described above is a medium containing no nitrogen (N) source for cell growth, or also referred to as N-free medium.

In another embodiment, the production medium of any of the embodiments described above includes a mixture of glycerol and vegetable oil as the carbon substrates to the microorganisms. In another embodiment the ratio of vegetable oil to glycerol ranges from about 1:25 to about 10:1, in another embodiment, from about 1:10 to about 5:1, and in another embodiment, from about 1:3 to about 1:1.

In still yet another embodiment, the sophorolipid producer produces a sophorolipid contained in a broth, the broth being further used to induce the celluslase producer to ultimately produce cellulase. The cellulase producer being optionally included in the broth prior to sophorolipid production or introduced at a later state.

In another embodiment, the culture in any of the embodiments described above includes a sophorolipid producer and a cellulase producer which are in the resting state or in the stationary phase of batch cultivation, also referred to as non-growing. For example, both sophorolipids and cellulase are secondary metabolites that are over-produced by non-growing cultures.

In another embodiment the method for producing cellulase further includes growing the sophorolipid producer and the cellulase producer separately, and mixing the sophorolipid producer and the cellulase producer to produce the culture before contacting or exposing the culture with the production medium. In an example embodiment, the method for producing cellulase further includes growing the *Candida bombicola* and the *Trichoderma reesei* separately, and mixing the *Candida bombicola* and the *Trichoderma reesei* to produce the culture before contacting the culture with the production medium.

In still yet another embodiment, the method for producing cellulose includes growing the two cultures separately with the sophorolipid producer in Reactor 1 and the cellulase producer in Reactor 2. The two reactors are then fed with the production media of different compositions. The production media for Reactor 1 is optimized for sophorolipid production and the production media for Reactor 2 is optimized for cellulase production. The two reactors are able to be maintained at different conditions, optimal for sophorolipid production and cellulase production, respectively. Next the resultant sophorolipid-containing broth in Reactor 1 is pumped to Reactor 2 at the desired rate, to induce cellulase production. In order to maintain a decent rate of production, the cells of sophorolipid producer in this broth can be removed (by filtration or centrifugation), deactivated (by heat or base addition), or not removed. The cells can be recycled within or back to Reactor 1. In one embodiment (broth removal), the cells removed from the broth are returned to Reactor 1, to minimize the need of growing more cells in Reactor 1. In another embodiment, the addition of the sophorolipid producer cells to Reactor 2 makes the Reactor 2 a co-culture of the two producers.

The above process is carried out in a continuous manner so that media are continuously fed to the two reactors, with the broth of Reactor 1 continuously pumped to Reactor 2, and a cellulase-containing product stream continuously collected from Reactor 2. Another embodiment includes the operation in either batch or semi-continuous operations. Still yet another embodiment involves the addition of the broth produced in Reactor 1 to a third reactor and combining the broth with the cellulase producer in the third reactor to produce the cellulase.

In one embodiment, the ratio of the sophorolipid producer to the cellulase producer in the second container ranges from about 0:1 to about 10:1. The 0:1 representing where all sophorolipid producer cells have been removed before the broth is added to the second container and the 10:1 corresponds to the situation where the sophorolipid producer cells are not removed.

As mentioned previous, this design has the benefit of additional control freedom to achieve optimized sophorolipid production and cellulase production simultaneously in two separate reactors. If only 1 reactor is used with the co-culture of the two producers, the medium design and operating conditions have to reflect the requirements between the two producers.

Figure 2:
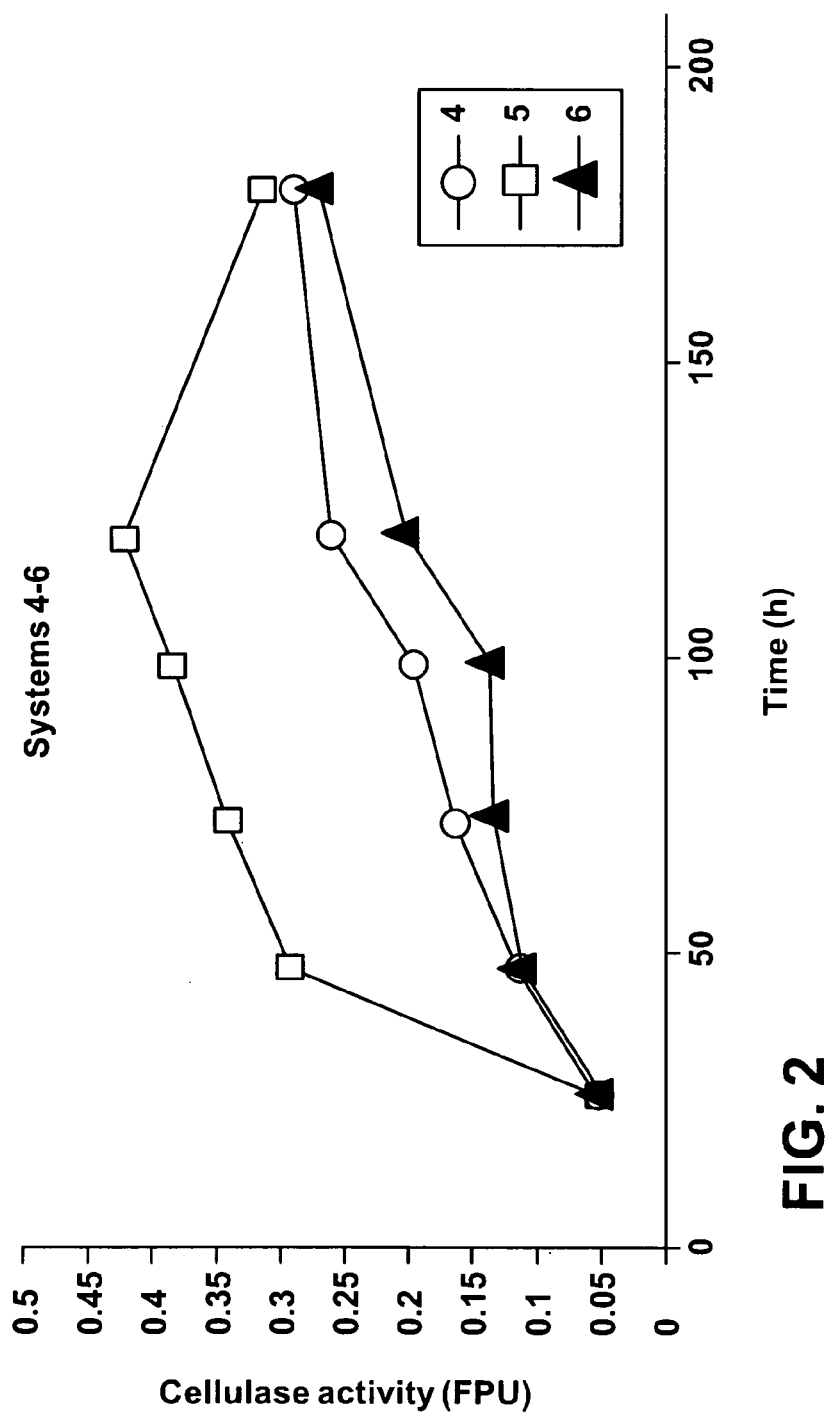
FIG. 2 provides plots of cellulase activity production from co-cultures of *Trichoderma reesei* and *Candida bombicola* in which the amount of *Trichoderma reesei* was approximately two times greater than the amount of *Candida bombicola*, according to an embodiment of the present invention.
Figure 3:
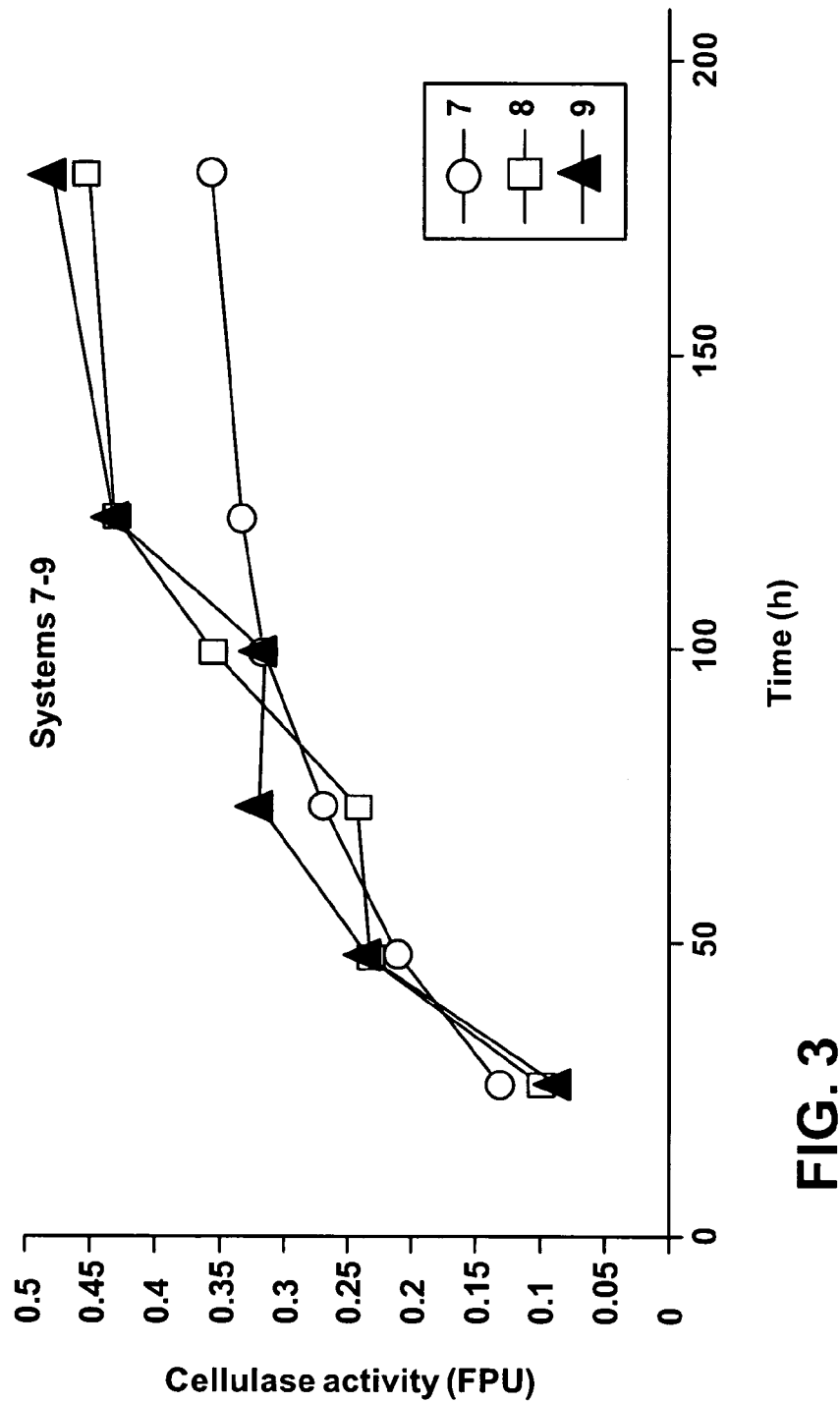
FIG. 3 provides plots of cellulase activity production from co-cultures of *Trichoderma reesei* and *Candida bombicola* in which the amount of *Trichoderma reesei* was approximately equal to the amount of *Candida bombicola*, according to an embodiment of the present invention.

FIGS. 1 through 3 detail plots of cellulase activity production from co-cultures of *Trichoderma reesei* and *Candida bombicola* in which the amount of *Trichoderma reesei* was approximately four times greater than the amount of *Candida bombicola*, two times greater than the amount of *Candida bombicola*, and approximately equal to the amount of *Candida bombicola*, respectively, according to various embodiments of the present invention. For each of the given ratios of the cellulase producer to sophorolipid producers, the amount of glycerol used in the mixture of carbon substrates was varied. The tests are described in the examples provided below. These results confirm the ability of the broth of *Candida bombicola* as an effective inducer of cellulase synthesis, presumably because the broth contains sophorolipids produced by *Candida bombicola*.

In another embodiment, the carbon substrates made available to the microorganisms are, for example, a mixture of glycerol and vegetable oil, such that the sophorolipid producer continuously converts these substrates to sophorolipids. The produced sophorolipids constantly induces the cellulase synthesis by the cellulase producer. The sophorolipids are also degraded and consumed by the cellulase producer. As a result, the sophorolipids and the glucose, if generated from their degradation, do not tend to accumulate to repressive levels in such systems, and the method for making the cellulase is stable.

In one example embodiment, the process for producing cellulase includes addition of the substrate at intermittent time intervals. For example, additional amounts of glycerol and/or vegetable oil may be added at several points along the production or method of producing cellulase.

In another embodiment, the process for producing cellulase includes continuous addition of the substrate component. For example, glycerol and/or vegetable oil may be added continuously to approximately match the consumption rate by the cells.

The following examples of processes for cellulase production according to embodiments of the present invention are further disclosed, and do not otherwise limit the scope of the invention.

Effective cellulase production in such systems is demonstrated:

Controls 1 and 2: Sophorolipid-Free Cultures

Cellulase production by the fungus *Trichoderma reesei* Rut C-30, a strain commonly used for industrial cellulase production, is measured. Two types of glycerol, by-products from a biodiesel manufacturing process, are used as the carbon substrate. In a first control sample, a crude grade of glycerol having approximately 85% glycerol is used as the carbon substrate, and a second control sample a purified (Kosher) grade of glycerol having 99.7% glycerol is used as the carbon substrate. In both samples, minimal cellulase production is observed. In 3 days, the maximal attainable cellulase activity was lower than 0.015 Filter Paper Unit (FPU), in both cases.

Controls 3 and 4: Sophorolipid Cultures

In another experiment, the fungus *Trichoderma reesei* Rut C-30 cells are grown for 1 day in the same two glycerol-based mediums described above. Broth containing 0.5 g/L of sophorolipids (for inducing the cellulase production) is then added. In 2 more days, the cellulase activity is found to reach about 0.047 FPU, which is 3 times higher than the 0.015 FPU reached in the sophorolipids-free controls. The small amount of sophorolipids added is found to be degraded and/or consumed within the first day of addition.

EXAMPLES 1-9

*Candida bombicola* and *Trichoderma reesei* Co-Cultures

Both sophorolipids and cellulase are secondary metabolites that are over-produced by non-growing cultures. The co-culture process is therefore designed to use resting (non-growing) cultures of *Candida bombicola* and *Trichoderma reesei*, by adding pre-grown cells to the media containing no N (nitrogen) source for growth. The experimental design is given in Table I:

TABLE I

|  |  | Example |  |  |  |  |  |  |  |  |
|---|---|---|---|---|---|---|---|---|---|---|
|  |  | 1 | 2 | 3 | 4 | 5 | 6 | 7 | 8 | 9 |
|  |  | System |  |  |  |  |  |  |  |  |
|  |  | 1 | 2 | 3 | 4 | 5 | 6 | 7 | 8 | 9 |
| Culture | *Trichoderma reesei* | 4 |  |  | 3.3 |  |  | 2.5 |  |  |
| (g/L) | *Candida bombicola* | 1 |  |  | 1.7 |  |  | 2.5 |  |  |
| Substrate | Glycerol | 5 |  |  |  |  |  |  |  |  |
| (g/L) | Vegetable oil | 2.5 | 5 | 10 | 2.5 | 5 | 10 | 2.5 | 5 | 10 |

The two cultures, *Candida bombicola* and *Trichoderma reesei*, are first grown separately in media for 72 hours and then harvested by centrifugation. The two cultures are then mixed at three different ratios, 4:1, 2:1 and 1:1, in the 9 simultaneous systems studied, as shown in Table 1. Note that the total cell concentration is kept the same at 5 g/L to minimize the differences in other uncontrolled factors, such as the dissolved oxygen levels in the broth and the pH changes due to cell metabolism. The N-free media used in all of the systems has the same concentration of glycerol (5 g/L) but three different concentrations of vegetable oil (2.5, 5.0 and 10 g/L; corresponding to 1:2, 1:1 and 2:1 ratio of vegetable oil-to-glycerol concentrations).

Samples are taken periodically and analyzed for cellulase activities (FPU), reducing sugars concentrations, and glycerol concentrations. The results of cellulase activities (FPU) are shown in FIG. 1. Cellulase production in all of these systems is much higher than that in the earlier experiment where 0.5 g/L of sophorolipids are added once in the stationary-phase culture of *Trichoderma reesei*. In addition, cellulase production is consistently higher in Systems 7-9 than in Systems 1-6. In Systems 7-9, the co-cultures have the higher (1:1) ratio of the sophorolipid-producer, *Candida bombicola*. The results thus confirm the ability of sophorolipids in effective induction for cellulase synthesis. The induction is particularly effective when the sophorolipids are continuously produced by *Candida bombicola* in the co-cultures. The results also appear to indicate higher cellulase production with a larger amount of vegetable oil in the medium. Nonetheless, the effects of vegetable oil-to-glycerol ratio can still be optimized. In all of the systems, glycerol is taken up and/or consumed by the cells within the first sampling period, i.e., 26 hours after the addition of cells to media.

Experiments Confirming Degradation of Sophorolipids by *Trichoderma reesei* Culture The following was performed to verify that sophorolipids are broken down by the cellulase producer, *Trichoderma reesei*, in order that sophorose can be released for inducing the cellulase production.

*Trichoderma reesei* is grown for 3 days in a medium containing 10 g/L of glycerol as the carbon substrate. This pre-grown culture is used to prepare the four different systems examined for sophorolipid degradation, as describe below. System (1) contains the cell-free supernatant collected by centrifugation, to remove the cells from a volume of the above pre-grown culture. System (2) is the same as System (1) except that 5 g/L of glycerol is added to the cell-free supernatant. System (3) is a volume of the cell-containing pre-grown culture broth. System (4) is the same as System (3) but supplemented with 5 g/L of glycerol. (Each of the above four systems is examined in duplicates, i.e., the whole experiment is conducted in 8 culture flasks.)

At the beginning of the degradation, about 1 g/L of sophorolipids are added to Systems (1) and (3), the systems without glycerol supplementation, and about 3 g/L of sophorolipids is added to Systems (2) and (4), the systems with glycerol supplementation. Samples are then taken periodically and analyzed for sophorolipid concentrations. The results are detailed in FIG. 4, where each data point represents the average of the duplicates for each system.

Figure 4:
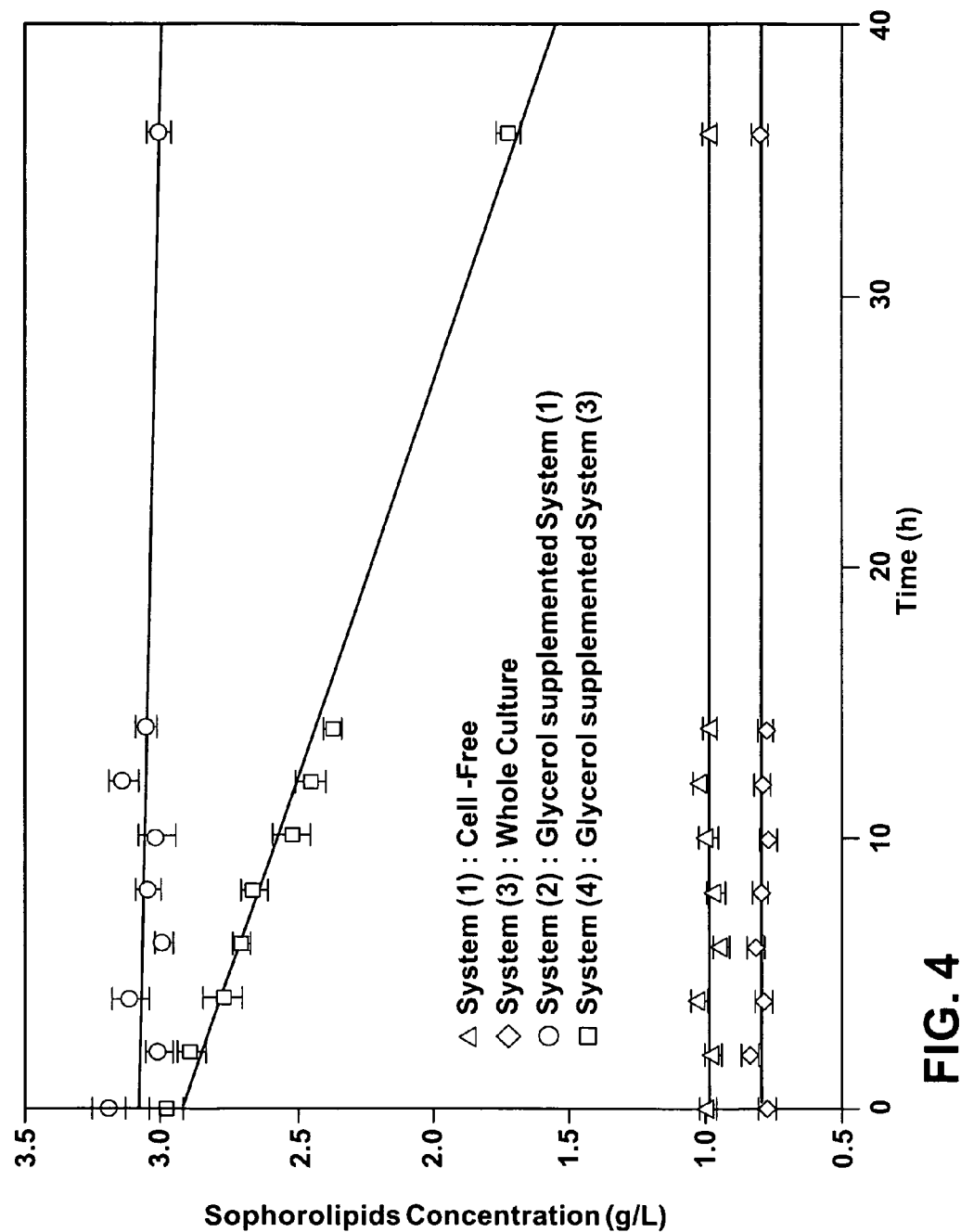
FIG. 4 details in one embodiment sophorolipid degradation by a *Trichoderma reesei* Rut C30 culture, with and without glycerol supplementation, and by the cell-free broth supernatant, with and without glycerol supplementation.

As shown in FIG. 4, the degradation of sophorolipids was observed clearly in System (4), with both *Trichoderma reesei* cells and glycerol, but not in other systems. The degradation was therefore cell-associated, not effected by extracellular enzymes in the broth supernatants. It is unclear why there was no sophorolipid degradation in the cell-containing broth without glycerol supplementation. Nonetheless, the ability of active *Trichoderma reesei* cells to degrade sophorolipids is verified. The rate of sophorolipid degradation in System (4) was approximately 0.04 g/L-h, corresponding to a specific degradation rate of 0.016 g sophorolipids/g dry cells-h.

The invention claimed is:
1. A method for producing cellulase comprising:
providing a culture comprising at least one sophorolipid producer and at least one cellulase producer;
providing at least one substrate supported on a production medium;
contacting the culture with the production medium and allowing the at least one substrate to be consumed by the at least one sophorolipid producer and the at least one cellulose producer to produce cellulase by consuming sophorolipids that are produced by the sophorolipid producer, wherein, in the step for contacting the culture with the production medium, a broth is produced that contains at least one sophorolipid produced by the at least one sophorolipid producer.

2. The method of claim 1 wherein the step of contacting the culture with the production medium promotes sophorolipid production without inhibiting or repressing cellulase production by more than 20%.

3. A method for producing cellulase comprising:
providing a culture comprising at least one sophorolipid producer and at least one cellulase producer;
providing at least one substrate supported on a production medium;
contacting the culture with the production medium and allowing the at least one substrate to be consumed by the at least one sophorolipid producer and the at least one cellulase producer to produce cellulase by consuming sophorolipids that are produced by the sophorolipid producer, wherein the production medium contains carbon substrates.

4. The method of claim 3 wherein the carbon substrates are provided at intermittent time intervals.

5. The method of claim 3 wherein the carbon substrates are provided continuously.

6. The method of claim 3 wherein the carbon substrate is one or more of:
glycerol, glucose, galactose, mannose, xylose, arabinose, lactose, sucrose, fructose, sorbose, maltose, cellobiose, amylase, amylopectin, dextrin, starch, glycogen, cellulose, polysaccharide, yeast extract, peptone, tryptone, an amino acid, peptide, a protein, milk, a fatty acid, glyceride, hydrocarbon, lipidic oil, vegetable oil, rapeseed oil, palm oil, oleic acid, linoleic acid, palmitic acid, lauric acid, a fat, alcohol, aldehyde, an ester, and ether amide.

7. The method of claim 1 wherein the production medium is selected to promote the production of one or more sophorolipids without inhibiting or repressing the production of cellulase by more than 20%.

8. The method of claim 7, wherein the production medium lacks at least one substrate essential for cell growth.

9. The method of claim 8, wherein the production medium is free of a nitrogen source.

10. The method of claim 1, wherein the sophorolipid producer is one or more of *Candida bombicola, Starmerella bombicola, Candida apicola, Rhodotorula bogoriensis*, and *Wickerhamiella domericqiae*.

11. The method of claim 1, wherein the cellulase producer is one or more of *Trichoderma reesei, Trichoderma viviride, Trichoderma longibrachiatum, Trichoderma lignorum, Aspergillus niger, Aspergillus terreus, Trametes trogii, Penicillium fellutanum, Penicillium hordei, Penicillium echinulatum, Aureobasidium pullulans, Rhizobium phaseoli, Humicola insolens, Piromyces communis, Clostridium thermocellum*, and *Thermomonospora fusca*.

12. The method of claim 1, wherein the culture is a non-growing culture.

13. The method of claim 1, wherein the ratio of the at least one sophorolipid producer to the at least one cellulase producer ranges from about 10:1 to about 1:25.

14. The method of claim 1, wherein the ratio of the at least one sophorolipid producer to the at least one cellulase producer ranges from about 5:1 to about 1:10.

15. The method of claim 1, wherein the ratio of the at least one sophorolipid producer to the at least one cellulase producer ranges from about 1:1 to about 1:4.

16. The method of claim 1, wherein the method further comprises:
growing the at least one sophorolipid producer separate from the at least one cellulose producer;
mixing the at least one sophorolipid producer and the at least one cellulase producer to produce the culture; and
subsequently contacting the culture with the production medium.

17. A method for producing cellulase comprising:
providing at least one sophorolipid producer in a first container;
providing at least one substrate supported on a production medium to the first container and allowing the at least one substrate to be consumed by the at least one sophorolipid producer to produce a broth;
providing at least one cellulase producer in a second container;
providing the broth from the first container to the second container to produce a culture and allowing the culture to produce cellulase.

18. The method of claim 17 wherein providing the broth from the first container to the second container further induces the at least one cellulase producer to produce cellulase.

19. The method of claim 17 wherein the cells of the at least one sophorolipid producer in the broth from the first container are removed before the broth is provided to the second container.

20. The method of claim 19 wherein the removed cells of the at least one sophorolipid producer are recycled back to the first container.

21. The method of claim 17 wherein the cells of the at least one sophorolipid producer are rendered inactive in the broth before the broth is provided to the second container.

22. The method of claim 17 wherein the method for producing cellulase is a continuous process.

23. The method of claim 17 wherein the method for producing cellulase is a batch process.

24. The method of claim 17 wherein the contacting the culture with the production medium promotes sophorolipid production without inhibiting or repressing cellulase production by more than 20%.

25. The method of claim 17, wherein the at least one sophorolipid producer is one or more of *Candida bombicola, Starmerella bombicola, Candida apicola, Rhodotorula bogoriensis*, and *Wickerhamiella domericqiae*.

26. The method of claim 17, wherein the at least one cellulase producer is one or more of *Trichoderma reesei, Trichoderma viviride, Trichoderma longibrachiatum, Trichoderma lignorum, Aspergillus niger, Aspergillus terreus, Trametes trogii, Penicillium fellutanum, Penicillium hordei, Penicillium echinulatum, Aureobasidium pullulans, Rhizobium phaseoli, Humicola insolens, Piromyces communis, Clostridium thermocellum*, and *Thermomonospora fusca*.

27. The method of claim 17, wherein the ratio of the at least one sophorolipid producer to the at least one cellulase producer in the culture formed in the second container ranges from 10:1 to 1:25.

28. A method for producing cellulase comprising:
providing at least one sophorolipid producer in a first container;
providing at least one substrate supported on a production medium to the first container and allowing the at least one substrate to be consumed by the at least one sophorolipid producer to produce a broth;
providing at least one cellulase producer in a second container;
providing the broth from the first container and the at least one cellulase producer from the second container to a third container to produce a culture and allowing the culture to produce cellulase.

* * * * *